United States Patent [19]

Kondow et al.

[11] 4,450,298
[45] May 22, 1984

[54] VAPOR PHASE CATALYTIC HYDROLYSIS OF BENZAL CHLORIDE OR ITS HALOGEN- OR TRIFLUOROMETHYL-SUBSTITUTE TO FORM BENZALDEHYDE OR SUBSTITUTE

[75] Inventors: Takeshi Kondow, Kamifukuoka; Koshi Okazaki, Saitama; Yutaka Katsuhara; Kimiaki Matsuoka, both of Kawagoe, all of Japan

[73] Assignee: Central Glass Company, Limited, Ube, Japan

[21] Appl. No.: 400,011

[22] Filed: Jul. 20, 1982

[30] Foreign Application Priority Data

Jul. 21, 1981 [JP] Japan .................................. 56-112977
Aug. 12, 1981 [JP] Japan .................................. 56-125374

[51] Int. Cl.³ .............................................. C07C 45/43
[52] U.S. Cl. ...................................... 568/437; 568/438
[58] Field of Search ................................ 568/437, 438

[56] References Cited

U.S. PATENT DOCUMENTS 4,277,421 7/1981 Landauer et al. ................ 568/437

FOREIGN PATENT DOCUMENTS

| 668217 | 8/1963 | Canada | 568/437 |
| 11281 | 5/1980 | European Pat. Off. | 568/437 |
| 2044832 | 3/1971 | Fed. Rep. of Germany | 568/437 |
| 766 | 2/1963 | Japan | 568/437 |
| 6129 | 2/1976 | Japan | 568/437 |
| 816253 | 7/1959 | United Kingdom | 568/437 |

*Primary Examiner*—Werren B. Lone
*Attorney, Agent, or Firm*—Fleit, Jacobson, Cohn & Price

[57] ABSTRACT

Vapor phase contact reaction between water and benzal chloride or a substitute expressed by $C_6H_{(5-n)}X_nCHCl_2$, wherein X representing a halogen atom or a trifluoromethyl group and n being 1 or 2, to form benzaldehyde or a substitute expressed by $C_6H_{(5-n)}X_nCHO$ can efficiently be achieved by using activated carbon treated with an acid such as sulfuric acid or impregnated with a metal chloride such as ferric chloride and/or a metal sulfate such as cupric sulfate as catalyst. The activated carbon catalyst long retains its high activity even when the starting material has trifluoromethyl group, which is liable to undergo partial decomposition with formation of hydrogen fluoride.

15 Claims, 1 Drawing Figure

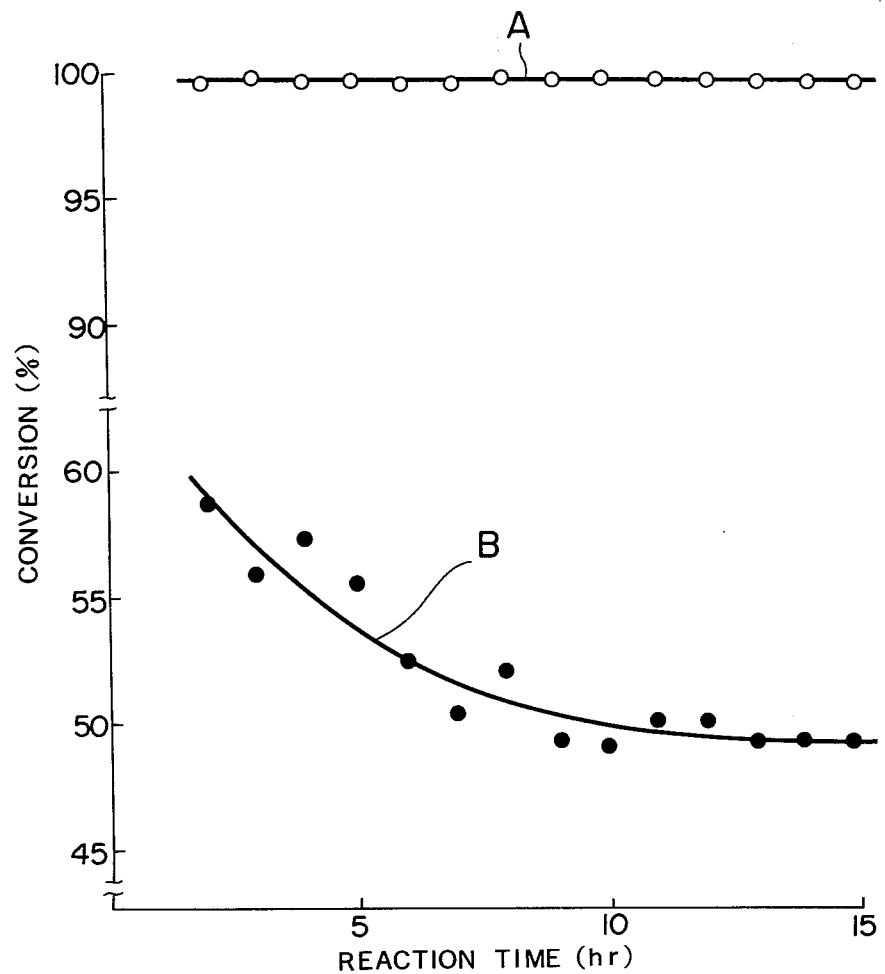

VAPOR PHASE CATALYTIC HYDROLYSIS OF BENZAL CHLORIDE OR ITS HALOGEN- OR TRIFLUOROMETHYL-SUBSTITUTE TO FORM BENZALDEHYDE OR SUBSTITUTE

BACKGROUND OF THE INVENTION

This invention relates to a process of preparing benzaldehyde or a substitute expressed by $C_6H_{(5-n)}X_nCHO$, wherein X represents a halogen atom or trifluoromethyl group and n is 1 or 2, by vapor phase catalytic reaction between water and benzal chloride or a substitute expressed by $C_6H_{(5-n)}X_nCHCl_2$.

Benzaldehyde and its substitutes of the above defined class are industrially of use as materials for the synthesis of various organic compounds including some medicines and agricultural chemicals. It is possible to obtain benzaldehyde or its substitute of the above defined class by hydrolysis of benzal chloride or its substitute of the above defined class, but it is impracticable to achieve the hydrolysis by merely heating a mixture of benzal chloride or its substitute with water because the hydrolysis proceeds only at a very low rate.

Accordingly various catalysts have been proposed for liquid phase hydrolysis of benzal chloride or its substitute to form benzaldehyde or its substitute. Typical examples of the hitherto proposed catalysts are as follows: (1) aqueous solution of acid or alkali; (2) cuprous chloride or cupric chloride; (3) aqueous solution of iron salt; (4) anhydrous zinc chloride; and (5) zinc oxide.

However, every process using one of these catalysts is disadvantageous in certain respects from an industrial point of view. More particularly, the use of an aqueous solution of an acid or an alkali (1) is liable to cause undesirable side reactions and, besides, is almost ineffective for the hydrolysis of substituted benzal chlorides having an electron attractive group typified by trifluoromethyl group. Furthermore, if this process is put into industrial practice it becomes a requisite to the process to use a reaction vessel of very large capacity relative to the quantity of the compound subjected to hydrolysis, and the waste acid or alkali must be treated with considerable trouble. Any one of the processes using the metal salt catalysts (2), (3) and (4) suffers from an unsatisfactorily low rate of reaction, and this problem becomes very serious when the starting material is a substituted benzal chloride having an electron attractive group, and an increase in the quantity of the metal salt catalyst with a view to enhancing the reaction rate significantly promotes unfavorable side-reactions. The use of zinc oxide catalyst (5) is almost ineffective for hydrolysis of a trifluoromethyl-substituted benzal chloride and, besides, is unsuitable to a continuous process because of the need for the step of separating zinc oxide from the reaction product.

Due to such problems or disadvantages, none of the hitherto proposed liquid phase catalytic hydrolysis processes can be taken as suitable to industrial practice.

Japanese Patent Application Primary Publication No. 48(1973)-5733 proposes a vapor phase catalytic reaction process for the hydrolysis of benzal chloride or its substitute characterized by using silica or alumina as catalyst either in pure state or in a state impregnated with cuprous chloride or cupric chloride. This process can be performed as a continuous process since the reaction takes place in vapor phase, but this process has the following shortcomings. In the case of using either silica or alumina in pure form as the catalyst, it is practically impossible to achieve the intended hydrolysis of a trifluoromethyl-substituted benzal chloride firstly because the rate of the reaction is very low even at an initial stage where the catalyst is in a fresh state, and secondly because the catalyst is easily fluorinated by hydrogen fluoride formed by hydrolysis of a portion of the trifluoromethyl group of the starting material and, therefore, is rapidly deactivated. Even in the case of using a silica or alumina catalyst impregnated with cuprous chloride or cupric chloride, the activity of the catalyst is insufficient for efficient hydrolysis of a trifluoromethyl-substituted benzal chloride and rapidly and significantly lowers with the lapse of time, so that the hydrolysis can hardly be performed as a truly continuous process.

SUMMARY OF THE INVENTION

It is an object of the present invention to provide a vapor phase catalytic hydrolysis process for the preparation of benzaldehyde or its halogen- or trifluoromethyl-substitute from benzal chloride or its halogen- or trifluoromethyl-substitute, which process is readily practicable as a continuous process and in which process the hydrolysis proceeds very rapidly without suffering from significant deactivation of the catalyst even when the starting material is a trifluoromethyl-substituted benzal chloride, so that the intended product is obtained with high purity and high yield.

A process according to the invention is for the preparation of a compound expressed by the general formula (I) and has the step of carrying out a vapor phase contact reaction between water and a compound expressed by the general formula (II) at an elevated temperature in the presence of a catalyst:

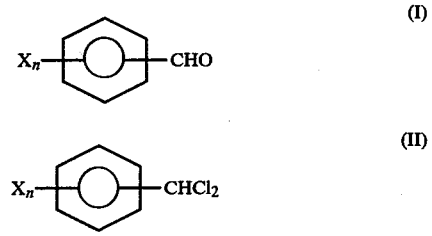

in both the formulas (I) and (II) X representing a halogen atom or a trifluoromethyl group, and n being 0, 1 or 2. As the improvement according to the invention, the catalyst comprises activated carbon as a fundamental components thereof.

More specifically, the catalyst in a process according to the invention is activated carbon treated with an acid, preferably with sulfuric acid, or activated carbon impregnated with a metal chloride typified by ferric chloride and/or a metal sulfate typified by cupric sulfate.

An activated carbon catalyst used in the present invention exhibits very high activity on the vapor phase hydrolysis of benzal chloride or its substitute of the above defined class even when the substitute has a strongly electron-attractive group typified by trifluoromethyl group and is high in boiling point and rather difficult to hydrolyze. Accordingly the intended hydrolysis reaction proceeds very rapidly, and therefore the hydrolysis operation can be performed rapidly in a reaction vessel of relatively small capacity. Furthermore, the activated carbon catalyst is scarcely influenced by hydrogen fluoride, which is formed by hydrolysis of a portion of the trifluoromethyl group in the starting material, and retains its high activity for a long period of time. Therefore, a high rate of conversion of benzal chloride or a substituted benzal chloride to the intended compound (I) can be attained irrespective of the kind of the starting compound (II). Because of these features, the invention is fully practicable as a continuous and industrial process with many advantages over the hitherto proposed processes.

BRIEF DESCRIPTION OF THE DRAWING

The single FIGURE is a graph showing the relationship between the reaction time and the conversion of the starting compound observed in an example of the invention and also in a comparative experiment.

DESCRIPTION OF THE PREFERRED EMBODIMENTS

Besides benzal chloride, the following compounds can be named as typical examples of substituted benzal chlorides useful in the process according to the invention: o-, m- or p-chlorobenzal chloride, o-, m- or p-bromobenzal chloride, o-, m- or p-fluorobenzal chloride, o-, m- or p-trifluoromethylbenzal chloride, 2,4-dichlorobenzal chloride, 2,5-dichlorobenzal chloride, 2,6-dichlorobenzal chloride, 2,4-dibromobenzal chloride, 2,5-dibromobenzal chloride and 2,6-dibromobenzal chloride.

By the process according to the invention benzal chloride and the above-named substituted benzal chlorides are hydrolyzed to the following compounds, respectively: benzaldehyde, o-, m- or p-chlorobenzaldehyde, o-, m- or p-bromobenzaldehyde, o-, m- or p-fluorobenzaldehyde, o-, m- or p-trifluoromethyl benzaldehyde, 2,4-dichlorobenzaldehyde, 2,5-dichlorobenzaldehyde, 2,6-dichlorobenzaldehyde, 2,4-dibromobenzaldehyde, 2,5-dibromobenzaldehyde and 2,6-dibromobenzaldehyde.

As to activated carbon for use in the process according to the invention, no particular restrictions are placed on its type, particle shape or particle size, and therefore it suffices for the purpose of the invention to use a commonly used and commercially available activated carbon.

In the case of treating activated carbon for use in the present invention with an acid, it is preferred to use sulfuric acid, hydrofluoric acid or phosphoric acid. In the state adsorbed and carried by activated carbon, any one of these acids exhibits a high catalytic activity on vapor phase hydrolysis of benzal chloride or a substituted benzal chloride. Since the vapor phase reaction in the method according to the invention is carried out at temperatures around 200° C. though the reaction temperature is varied depending on the kind of the compound used as the starting material, it is most preferable to choose an acid the boiling point of which is above the intended reaction temperature. Sulfuric acid is a typical example of acids which meet this requirement. Besides, sulfuric acid is a readily available industrial material relatively low in price and relatively easy to handle. Therefore, sulfuric acid is the most preferred acid for treatment of activated carbon in the present invention.

An activated carbon catalyst prepared by treatment with a preferred acid exhibits a very high catalytic activity in the hydrolyzing reaction in the process of the invention. In the presence of this catalyst, a contact reaction between steam and vaporized benzal chloride or a substituted benzal chloride proceeds very rapidly even when the starting compound has a strongly electron-attractive group typified by trifluoromethyl group, and it is possible to carry out the reaction as a continuous process. Furthermore, the activity of this catalyst hardly lowers even when hydrogen fluoride is formed in the reaction system by hydrolysis of a portion of the trifluoromethyl group of the starting compound, and therefore this catalyst retains its very high activity for a very long period of time.

The acid treatment of activated carbon can be performed under various conditions insofar as the surface regions of the activated carbon particles can sufficiently be impregnated with the acid. From the viewpoint of surface activity, it is suitable to employ a relatively high acid concentration. In the case of treatment with sulfuric acid for example, it is suitable to use 95% (by weight) or more concentrated sulfuric acid. Both the temperature of the sulfuric acid solution and the immersion time to achieve the acid treatment of activated carbon can freely be determined. A practical range of the temperature is from room temperature to the boiling point of the employed sulfuric acid solution, and an immersion time of a few hours suffices for the purpose. For convenience of handling, the activated carbon after the acid treatment is washed with water and then dried at about 80°–100° C.

In the case of using an activated carbon catalyst impregnated with a metal chloride and/or a metal sulfate, it is preferred to make a selection from the following compounds: manganese dichloride, ferric chloride, cobalt dichloride, nickel dichloride, palladium dichloride, cupric chloride, zinc chloride, tin dichloride, ferrous sulfate and cupric sulfate. In the state adsorbed and carried by activated carbon, any one of these metal salts exhibits a very high catalytic activity on vapor phase hydrolysis of benzal chloride and substituted benzal chlorides including those which have a strongly electron-attractive group typified by trifluoromethyl group and are high in boiling point and rather difficult to hydrolyze. Furthermore, an activated carbon catalyst of this type exhibits only a very small extent of lowering in its activity with the lapse of time and long retains its activity even when used in a reaction system in which hydrogen fluoride is formed by a side-reaction.

As to the method of impregnating activated carbon with a metal chloride and/or a metal sulfate, a free choice can be made from known impregnating methods. However, usually it is convenient and suitable to employ an immersion method in which the activated carbon for treatment is kept immersed in an aqueous solution of a selected metal salt for a period of time ranging from a few hours to one day, followed by air-drying at about 80°–100° C. The temperature of the solution during the immersion is not specified, and usually it suffices to leave the solution at room temperature. When it is intended to impregnate activated carbon with a relatively large amount of a metal sulfate which is generally low in solubility in water, it is suitable to perform the immersion treatment by adequately heating the sulfate solution.

It is preferred that the total amount of the metal chloride and/or metal sulfate carried by activated carbon is in the range from 10 to 40% by weight of the activated carbon, firstly because the catalytic activity of the activated carbon impregnated with the metal salt is not always sufficiently high when the total amount of the metal salt is less than 10% by weight of the activated carbon and secondly because an increase in the amount of the metal salt beyond 40% by weight hardly results in a corresponding enhancement of the catalytic activity. The concentration of the metal salt solution may suitably be determined based on the desired amount of the metal salt to be carried by the activated carbon.

The process according to the invention can be performed as a continuous process generally in the following way.

As the first step, water and benzal chloride or a substituted benzal chloride are introduced into a heated vaporizer respectively at predetermined flow rates by using metering pumps to thereby vaporize the both materials. The temperature in the vaporizer should be above the boiling point of the compound to be hydrolyzed, and is determined such that a complete vapor phase may be maintained during the subsequent catalytic hydrolysis step with consideration of the feed rates of the materials relative to the capacity of the vaporizer. Another matter for consideration in determining the vaporizing temperature is to avoid significant evaporation of the acid or sublimation of the metal salt contained in the activated carbon catalyst during contact of the heated mixed gas with the catalyst. In general, a suitable range of the vaporizing temperature is from about 200° C. to about 340° C.

The mixed gas prepared in the vaporizer is passed through a column packed with a selected activated carbon catalyst, which is kept heated at a temperature sufficient to maintain the supplied reactants in vapor phase but not so high as will cause significant evaporation of the acid or sublimation of the metal salt contained in the catalyst. In general the catalyst column is maintained at a temperature in the range from about 150° to 200° C. in the case of using an activated carbon catalyst treated with acid, and in the range from about 100° to 300° C. in the case of an activated carbon catalyst impregnated with a metal chloride or a metal sulfate. During contact with the packed catalyst, benzal chloride or the substituted benzal chloride contained in the mixed gas is hydrolyzed by reaction with steam in the mixed gas.

As to the mole ratio of steam to the vaporized benzal chloride or substituted benzal chloride in this continuous process, it is suitable to use about one mole of water (steam) per each —$CHCl_2$ group in the compound to be hydrolyzed from a stoichiometric viewpoint. In practice, however, it is suitable to use 5 to 10 moles of water (steam) per each —$CHCl_2$ group. A preferred range of the flow rate of the mixed gas through the packed catalyst column is from 0.15 to 1.5 $hr^{-1}$ in terms of liquid hourly space velocity. A practically complete reaction can be achieved by determining the flow rate of the mixed gas and the length of the catalyst column such that the contact reaction time becomes from several seconds to tens of seconds. Usually, a contact reaction time ranging from about 2 to 20 sec is sufficient and preferable.

Benzaldehyde or a substituted benzaldehyde formed by this continuous hydrolysis reaction is passed through a cooler provided at the lower end of the reaction tube together with the unreacted portion of the steam and received in a suitable vessel in a cooled and condensed state. In most cases the compound as the reaction product is obtained in a state separated from the water (condensate of the unreacted steam), but in some cases the reaction product remains in a state suspending in water. In the latter cases the reaction product can be isolated by a simple solvent extraction method using a suitable organic solvent. The reaction product can be refined by a vacuum distillation method.

The invention will be illustrated by the following examples 1–3 relating to the use of activated carbon catalyst treated with acid and examples 4–15 relating to the use of activated carbon catalyst impregnated with a metal chloride or a metal sulfate.

EXAMPLE 1

An activated carbon catalyst was prepared by the steps of immersing a commercially available activated carbon, which passed through a 4-mesh sieve and retained on a 10-mesh sieve, in 95% sulfuric acid for 2 hr at room temperature, washing the activated carbon withdrawn from the acid and air-drying the washed activated carbon at 80° C. for 3 hr. In a reaction tube a packed catalyst column was provided by packing 25 ml of the acid-treated activated carbon catalyst in a section of the reaction tube.

Water and benzal chloride were continuously introduced into a vaporizer by using metering pumps, respectively. The feed rate of water was 0.37 g/min, and that of benzal chloride was 0.33 g/min. The vaporizer was maintained at 230° C. and connected to the aforementioned reaction tube, in which the packed catalyst column was kept heated at 180° C.

While the mixed gas discharged from the vaporizer passed through the packed catalyst column, the vaporized benzal chloride and steam in the mixed gas underwent a catalytic contact reaction. The reacted gas was condensed in a cooler to obtain a liquid suspension, and the suspension was subjected to ether extraction. The extract was dried, deprived of ether by distillation and then subjected to reduced-pressure distillation in a nitrogen gas atmosphere.

The above described process was continued until the quantity of benzal chloride subjected to reaction reached 100 g. Obtained as the result was 64.0 g of benzaldehyde containing no trace of tar as a possible by-product. The yield of benzaldehyde was 97.2% of theory.

EXAMPLE 2

The activated carbon mentioned in Example 1 was immersed in 95% sulfuric acid kept heated at 150° C. for 3 hr, then washed with water and air-dried at 100° C. for 3 hr. In a reaction tube a packed catalyst column was provided by packing 25 ml of the thus treated activated carbon in a section of the tube.

In a vaporizer maintained at 250° C., 0.19 g/min of water and 0.21 g/min of m-chlorobenzal chloride were continuously vaporized. The resultant mixed gas was passed through the packed catalyst column which was kept heated at 200° C. to cause catalytic contact reaction between the vaporized m-chlorobenzal chloride and steam in the mixed gas.

The reaction was continuously carried out until the quantity of reacted m-chlorobenzal chloride reached 100 g. Obtained as the result was 69.1 g of m-chlorobenzaldehyde containing no trace of tar. The yield of m-chlorobenzaldehyde was 96.2% of theory.

EXAMPLE 3

Using the activated carbon catalyst described in Example 2 and under the same conditions as in Example 2, 0.18 g/min of water and 0.23 g/min of o-trifluoromethylbenzal chloride were continuously vaporized and passed through the packed catalyst column to accomplish hydrolysis of 100 g of o-trifluoromethylbenzal chloride in total.

This process gave 71.0 g of o-trifluoromethyl benzaldehyde containing no trace of tar, so that the yield was 93.5% of theory. The boiling point of this product was 82°–83° C. at 40 mmHg.

REFERENCE 1

For comparison with Example 3, use was made of 50 ml of a catalyst prepared by firing $\gamma$-$Al_2O_3$ at 400° C. for 5 hr in place of 25 ml of the acid-treated activated carbon in Example 3. In other respects the vapor phase hydrolysis process of Example 3 was performed identically.

In this case, the conversion of o-trifluoromethylbenzal chloride to o-trifluoromethyl benzaldehyde was about 25% when examined after the lapse of 1 hr from the start of the continuous reaction and lowered to only about 5% after the lapse of additional 5 hr.

REFERENCE 2

In place of the acid-treated activated carbon used in Example 3, use was made of 25 ml of the activated carbon mentioned in Example 1 without treating it with any acid or any alternative. In other respects the vapor phase hydrolysis process of Example 3 was performed identically.

When the quantity of o-trifluoromethylbenzal chloride subjected to the reaction reached 100 g, the conversion of this compound to o-trifluoromethyl benzaldehyde was only 1.5%.

The process of Reference 2 was repeated generally similarly but by raising the reaction temperature to 350° C. and extending the reaction time by 300 percent. In this case the conversion value increased to 34.7%, but it was found that phthalic acid was formed as a by-product due to the employment of a very high reaction temperature.

EXAMPLE 4

An activated carbon catalyst was prepared by the steps of immersing the activated carbon mentioned in Example 1 in a 20% (by weight) aqueous solution of ferric chloride for 24 hr at room temperature and air-drying the activated carbon withdrawn from the solution at 80° C. for 3 hr. In this catalyst, the amount of ferric chloride was 16% by weight of the activated carbon.

The continuous vapor phase hydrolysis process of Example 1 was performed generally similarly but by using 25 ml of the chloride-containing catalyst prepared by the above described steps in place of the acid-treated activated carbon in Example 1.

The reaction was continuously carried out until the quantity of benzal chloride subjected to reaction reached 100 g. As the result 64.1 g of benzaldehyde was obtained, so that the yield was 97.4% of theory.

EXAMPLE 5

The continuous vapor phase hydrolysis process of Example 2 was performed generally similarly except that 25 ml of the chloride-containing activated carbon catalyst described in Example 4 was used in place of the acid-treated activated carbon in Example 2.

The reaction was continuously carried out until the quantity of m-chlorobenzal chloride subjected to reaction reached 100 g. As the result 69.0 g of m-chlorobenzaldehyde was obtained, so that the yield was 96.0% of theory.

EXAMPLES 6–14

In these examples, the continuous vapor phase hydrolysis process of Example 3 was repeated generally similarly except that the acid-treated activated carbon in Example 3 was replaced by different activated carbon catalysts in the respective examples as shown in the following Table. In every example the reaction was continued until the quantity of o-trifluoromethylbenzal chloride subjected to reaction reached 100 g. The yield values of o-trifluoromethyl benzaldehyde in Examples 6–14 are also presented in the Table.

| | Metal Salt in Activated Carbon Catalyst | Yield of o-Trifluoromethyl benzaldehyde | |
|---|---|---|---|
| | | Weight | % of theory |
| Example 6 | $SnCl_2$, 33 Wt % of activated carbon | 65.0 g | 85.5% |
| Example 7 | $NiCl_2$, 19 Wt % of activated carbon | 63.3 g | 83.4% |
| Example 8 | $ZnCl_2$, 35 Wt % of activated carbon | 66.8 g | 87.9% |
| Example 9 | $CuCl_2$, 35 Wt % of activated carbon | 69.9 g | 92.0% |
| Example 10 | $MnCl_2$, 32 Wt % of activated carbon | 72.1 g | 94.9% |
| Example 11 | $CoCl_2$, 25 Wt % of activated carbon | 72.9 g | 95.9% |
| Example 12 | $FeCl_3$, 16 Wt % of activated carbon | 73.0 g | 96.1% |
| Example 13 | $FeSo_4$, 14 Wt % of activated carbon | 52.6 g | 69.2% |
| Example 14 | $CuSO_4$, 12 Wt % of activated carbon | 70.0 g | 91.9% |

EXAMPLE 15

In accordance with Example 4, the activated carbon was impregnated with ferric chloride such that the amount of ferric chloride in the resultant catalyst was 16 wt% of the activated carbon, and 25 ml of this catalyst was packed in a reaction tube to provide a packed catalyst column.

In a vaporizer kept heated at 250° C., 16 g/hr of water and 20 g/hr of o-trifluoromethylbenzal chloride were continuously vaporized. The resultant mixed gas was passed through the packed catalyst column which was kept heated at 200° C. The vapor phase catalytic contact reaction was continuously carried out for 15 hr.

The conversion of o-trifluoromethylbenzal chloride to o-trifluoromethyl benzaldehyde was examined at various time points during the total reaction time of 15 hr. In the single FIGURE, the curve A represents the result of the examination.

REFERENCE 3

A catalyst was prepared by the steps of immersing $\gamma$-$Al_2O_3$ in a solution of 160 g of $CuCl_2.2H_2O$ in 160 g of water kept heated at 90° C. for 2 hr, and heating the alumina withdrawn from the solution at 400° C. for 2 hr. In this catalyst the amount of cupric chloride was 28.0% by weight of $\gamma$-$Al_2O_3$.

The process of Example 15 was performed generally similarly except that 25 ml of the alumina base catalyst prepared in the above described way was used in place of the activated carbon catalyst in Example 15.

The conversion of o-trifluoromethylbenzal chloride to o-trifluoromethyl benzaldehyde was examined in the same manner as in Example 15. The result is represented by the curve B in the FIGURE.

From a comparison between the curves A and B, it is apparent that the alumina base catalyst in Reference 3 was very low in its catalytic activity on the vapor phase hydrolysis of o-trifluoromethylbenzal chloride and, furthermore, underwent a very significant deterioration in its activity with the lapse of time.

What is claimed is:

1. In a process of preparing a compound expressed by the general formula (I), the process having the step of carrying out a vapor phase contact reaction between water and a compound expressed by the general formula (II) at an elevated temperature in the presence of a catalyst,

(I)

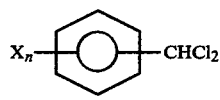
(II)

in both the formulas (I) and (II) X representing a halogen atom or a trifluoromethyl group and n being 0, 1 or 2,
the improvement comprising said catalyst comprising activated carbon treated with an inorganic acid selected from the group consisting of sulfuric acid, hydrofluoric acid and phosphoric acid.

2. A process according to claim 1, wherein said elevated temperature is in the range from about 150° C. to about 200° C.

3. A process according to claim 1, wherein said catalyst is activated carbon treated with sulfuric acid.

4. A process according to claim 3, wherein the concentration of said sulfuric acid is at least 95% by weight.

5. A process according to claim 1, wherein the vapor phase contact reaction is carried out by passing a mixture of said compound (II) in vapor phase and steam through a column packed with said catalyst.

6. A process according to claim 5, wherein the amount of said steam is 5 to 10 moles per each —CHCl$_2$ group in said compound (II) in said mixture.

7. A process according to claim 5, wherein said mixture is passed through said column such that said mixture is in contact with said catalyst for 2 to 20 seconds.

8. A process according to claim 1, wherein said compound (II) is selected from the group consisting of benzal chloride, o-, m- or p-chlorobenzal chloride, o-, m- or p-bromobenzal chloride, o-, m- or p-fluorobenzal chloride, o-, m- or p-trifluoromethylbenzal chloride, 2,4-dichlorobenzal chloride, 2,5-dichlorobenzal chloride, 2,6-dichlorobenzal chloride, 2,4-dibromobenzal chloride, 2,5-dibromobenzal chloride and 2,6-dibromobenzal chloride.

9. In a process of preparing a compound expressed by the general formula (I), the process having the step of carrying out a vapor phase contact reaction between water and a compound expressed by the general formula (II) at an elevated temperature in the presence of a catalyst,

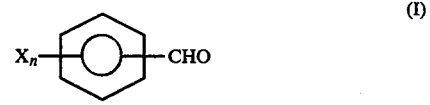
(I)

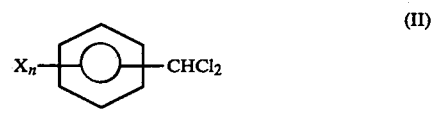
(II)

in both the formulas (I) and (II) X representing a halogen atom or a trifluoromethyl group and n being 0, 1 or 2,
the improvement comprising said catalyst comprising a metal chloride carried on an activated carbon.

10. A process according to claim 9, wherein said metal chloride is selected from the group consisting of manganese dichloride, ferric chloride, cobalt dichloride, nickel dichloride, palladium dichloride, cupric chloride, zinc chloride and tin dichloride.

11. A process according to claim 10, wherein the amount of said metal chloride is in the range from 10 to 40% by weight of said activated carbon.

12. In a process of preparing a compound expressed by the general formula (I), the process having the step of carrying out a vapor phase contact reaction between water and a compound expressed by the general formula (II) at an elevated temperature in the presence of a catalyst,

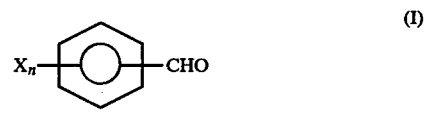
(I)

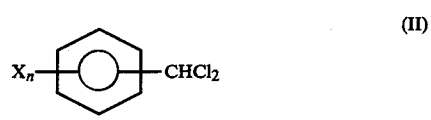
(II)

in both the formulas (I) and (II) X representing a halogen atom or a trifluoromethyl group and n being 0, 1 or 2,
the improvement comprising said catalyst comprising a metal sulfate carried on an activated carbon.

13. A process according to claim 8, wherein said metal sulfate is selected from the group consisting of ferrous sulfate and cupric sulfate.

14. A process according to claim 13, wherein the amount of said metal sulfate is in the range from 10 to 40% by weight of said activated carbon.

15. A process according to claim 9 or 12, wherein said elevated temperature is in the range from about 100° C. to about 300° C.

* * * * *